United States Patent [19]

Scroggins et al.

[11] Patent Number: 5,742,063
[45] Date of Patent: Apr. 21, 1998

[54] AIR SANITIZER ATTACHMENT FOR AIR DUCTS

[76] Inventors: William Henry Scroggins, 5639 Silvian Rd., W. Palm Beach, Fla. 33415; Charles Philip Hawkins, 933 Almeria Rd., West Palm Beach, Fla. 33405

[21] Appl. No.: 766,929

[22] Filed: Dec. 16, 1996

Related U.S. Application Data

[63] Continuation-in-part of Ser. No. 519,963, Aug. 28, 1995, abandoned.

[51] Int. Cl.⁶ ............................................. G01N 23/00
[52] U.S. Cl. ............................... 250/455.11; 250/453.1
[58] Field of Search ........................ 250/455.11, 493.1, 250/504 H, 436

[56] References Cited

U.S. PATENT DOCUMENTS

| | | | |
|---|---|---|---|
| 3,970,856 | 7/1976 | Mahaffey et al. | 250/504 H |
| 3,971,968 | 7/1976 | Bachmann et al. | 315/108 |
| 4,629,896 | 12/1986 | Bridgen | 250/455.11 |
| 4,835,442 | 5/1989 | Sugimoto et al. | 313/565 |
| 4,896,042 | 1/1990 | Humphreys | 250/504 H |
| 4,900,253 | 2/1990 | Landis | 250/504 H |
| 4,983,846 | 1/1991 | Rois | 250/455.11 |
| 5,219,534 | 6/1993 | Reynolds | 422/186.3 |
| 5,334,347 | 8/1994 | Hollander | 250/455.11 |

*Primary Examiner*—Bruce Anderson
*Attorney, Agent, or Firm*—John P. Halvonik

[57] ABSTRACT

A sterilizing unit for air ducts having an aluminum housing and at least one UV emitting probe extending downward into the duct. The upper surface of the unit overhangs the side walls for easy installation into the duct. At least one UV emitting probe in connection with the circuitry extends downward into the air duct. There is a light sensor, or monitor, that extends from the upper side of the unit to a point near the probe in order to provide a visual indication of the condition of the UV probe without exposure to the UV light. An on/off switch on the upper surface of the device allows for safety in servicing the sterilizing unit.

2 Claims, 1 Drawing Sheet

AIR SANITIZER ATTACHMENT FOR AIR DUCTS

AIR SANITIZER ATTACHMENT FOR AIR DUCTS; A continuation in part of Ser. No. 08/519,963 filed Aug. 28, 1995 now abandoned.

BACKGROUND AND FIELD OF THE INVENTION

The invention relates to the field of sterilizing and cleaning and, in particular, to a such a device having ultra violet (UV) radiation emitting probes, and that is designed for retrofit installation into air ducts in commercial and domestic settings.

Sterilizing air and killing bacteria, viruses, mold, and yeast in air have become health care concerns in recent times. Legionnaire's disease is one such disease believed to be related to poor air quality and is thought to be linked to bacteria allowed to exist in air ducts. The use of UV emitting probes is thought to produce radiation that kill bacteria and hence sterilize the air. It is believed that UV radiation is effective at killing bacteria in an air sterilization unit.

The purpose of the invention is to allow a device to be easily retrofitted onto existing air ducts in a manner that does not require large expenditure of effort or reconstruction of air duct. Once the device is attached it will destroy germs, mold, mildews, spores, and viruses found in the air in air conditioning or similar airway systems.

Such UV powered probes need to have a constant power supplies if they are to be in continuous usage. The device described herein is able to utilize UV probes with a higher UV power radiation than similar lamps. It is thought that the use of higher UV power probes will be beneficial to such units and enable them to kill all or a large portion of the airborne bacteria.

It is thought that by having an on/off switch on the outside of the unit where it is accessible for the home owner or maintenance person would allow one to activate the UV bulb without exposure to the high radiation from the UV sources.

Having a light sensor monitor on the outside of the device is thought beneficial to allow the homeowner, etc. to periodically check the condition of the probe and service it if necessary. It is thought important to have an easy to read monitor that does not require UV exposure or removal from the air duct to see if it is in operation.

DESCRIPTION OF THE PRIOR ART

While there are devices that sterilize air ducts using UV radiation, such devices typically utilize UV emitting probes that are basically straight and have electrical contacts at both ends of the probe. These probes are limited in the amount of power and the amount of UV radiation that they can emit. The fixture described herein uses one or more UV tubes (probes) that are of double tube design and thus have both electrical contacts at one end of the probe.

Utilizing such double tube probes is thought to be an advantage over straight probes because the electrical connections can be made by one common socket at one end of the probe. This permits easy serviceability, efficient wiring and a higher concentration of UV radiated power. Long straight tubes typically must be wiped free of dust more frequently than those of the present invention.

The use of single connection for the tube makes it easier to remove and replace the tube. The use of double tube quartz tube would hang vertically in the duct and tend to build up less dust and need less frequent cleaning. The use of a single connection also decreases the chance for breakage of the tube during removal.

The fixture shown and described here can fit into much smaller air ducts because of the design of the probe and housing. The light sensors allowing easy determination of whether the probe is on is also believed to be novel. The use of a on/off button on the upper surface of the housing where it can be easily accessed is also though to be novel. A sliding removable top on the unit allows free access for servicing the unit and this is also thought to be novel, along with the unique extruded aluminum housing. The use of the aluminum housing is believed to have advantages over prior art in that such material provides an excellent heat sink for the ballast and probes and therefore prolongs the life of such components.

SUMMARY OF THE INVENTION

A sterilizing unit for air ducts having an aluminum housing of substantially rectangular shape and cross section so as to enclose circuitry, etc. associated with UV emitting probes (lamps). The upper surface has a flange in connection with said housing and that overhangs the side walls of the housing for easy installation. There is at least one UV emitting probe is in connection with the circuitry and the unit has a passageway in the underside for the UV emitting probes to extend downward into the air duct. There is a light sensor, or monitor, comprised of light transmission material that extends from the upper side of the unit to a point near the probe in order to provide a visual indication of the condition of the UV probe without exposure to the UV radiation. An on/off switch on the upper surface of the device allows the bulbs to be activated.

It is an object of the invention to provide an air sterilizing device having a means for monitoring the present condition of the UV emitting probe without the user having to remove the unit from the air duct or exposure to high UV radiation.

It is an object of the invention to provide a power cut off for UV emitting sterilizing device switch that is readily accessible to a service person.

Another object of the invention is to have a sterilizing system that can be readily attached to an air duct with a minimum of modifications to the duct.

Another object of the invention is to provide a UV emitting sterilizing probe in an airway system that can safely utilize a low consumption of electric power without danger to the unit or to the electrical system in the building or home.

Other advantages will become known to those skilled in the art once the invention is shown and described.

DESCRIPTION OF THE PREFERRED EMBODIMENT

Figure 1:
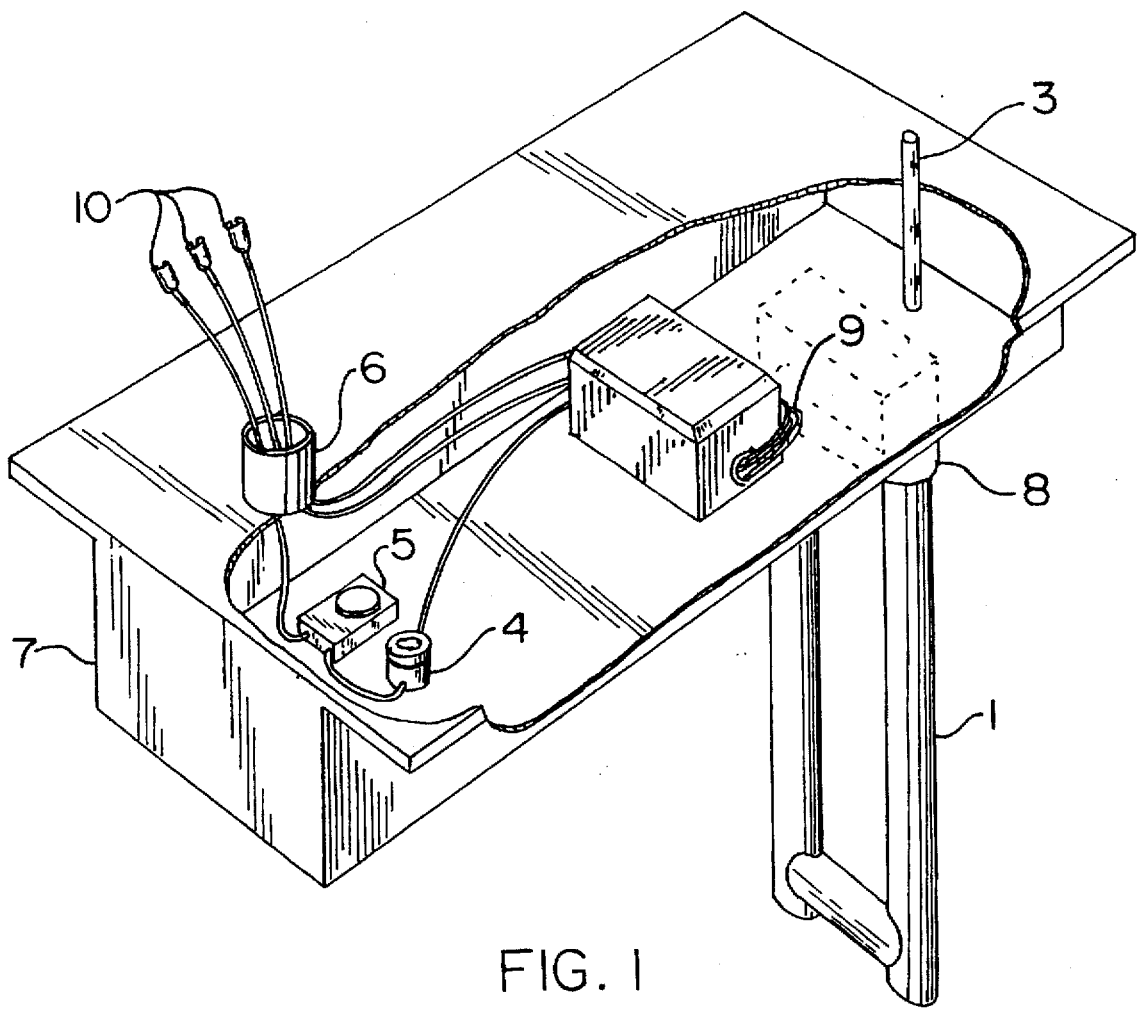
FIG. 1 Shows overall construction of the apparatus.

The main body 7, or housing, of the device is of rectangular shape and having an approximately one inch overhang on the upper surface of the housing. Preferably the housing will have an overhanging upper wall 12 that extends over two sides of the unit. The overhang could also overhang all four sides but this is not essential. This design is used for an easier installation and does not allow the fixture to move around once installed. The housing stores electrical circuitry associated with the probe(s) 1 and supports the probe(s) as they extend downward into the duct. It is preferred that the housing be made of aluminum material.

The UV probes (lamps) are supported by a lamp fixture 8 attached to the bottom wall of the housing and the probe(s) hang down from the fixture. These lamps will produce a very strong germicidal radiation in the duct work so as to kill any microorganisms that might pass through. Because of the danger of UV exposure to a user, the fixture has a light transmitting sensor at each end so that the installer can tell if the probes are working without having to remove the fixture from the duct work and without having to look directly at such light.

The UV probes themselves vary in length depending on the size of the system being treated and will give maximum killing power because they are connected only at one end by the power supply. These probes may be to different specifications depending upon the different applications and needs of the application. It is preferred that the lamps be of single ended, "double tube design i.e. each bulb has electrical connections at one end of the bulb only so that the electrical connections for such need only be on one side of the lamp. Thus, the electrical connections for each end of the lamp are found in the one socket on the underside of the housing.

The fixture also has an on/off switch 5 and is fused to be able to cut itself off in the event of power problems. An air flow turbulator or fan may be installed up to three feet away from the fixture in order to cause the air to swirl and mix with the germ killing rays of the probes. Power supply lines 10 comes out of the top of the fixture along with the fuse holder 4 and the on/off switch 5 so that no one is exposed directly to the UV probes when they are servicing the device.

A monitoring device 3 may be used in order for an observer on the outside of the duct to observe whether the light is on. The monitor should extend the entire thickness of the unit from the upper surface to the lower surface. The monitor should comprise a light transmission material that can transmit the UV light on the underside of the monitor back up to the upper side. An observer on the upper side could look at the top of the unit from outside the duct and determine whether the light is on by viewing the monitor.

The housing 7 which should be of generally rectangular shape and preferably made of aluminum. The main portion is of square cross section and of size sufficient to hold the electrical components such as the fuse, on/off switch, ballasting circuit 2, probe and other associated electrical connections among the elements. An insulator in the form of a grommet is shown at 9. Any state of the art insulation material would due for this piece.

The underside of the housing should have space sufficient to support at least one UV emitting probe in a fixture. The fixture would be connected to a portion of the underside of the unit. The probe should extend downward from the underside and extend down into the air duct. The upper surface of the unit should be of larger area than that of the underside so that the upper surface will overlap the side walls of the main portion and provide an overhang or flange. This upper surface has a portion 12 that should overhang the side walls of the main unit by about 1–2" on each side.

Figure 2:
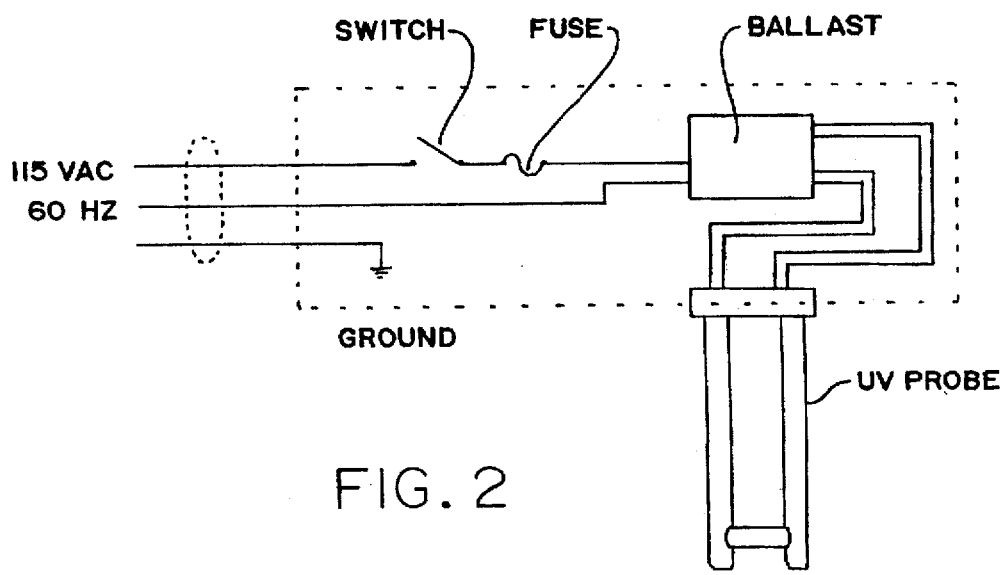
FIG. 2 Possible electrical schematic.

The internal circuitry should include a fuse 4 and an on/off switch in connection with the electric power supply to the UV probe. A ballasting 2 may be housed inside of housing 9. This type of circuit provides proper voltage for the initial activation of the UV probe. A passage 6 in the upper surface of the unit provides access for electric power lines. Such power lines may be connected a power supply such as an electric wall outlet, etc. FIG. 2 illustrates one such electrical wiring set up for the device.

The on/off button 4 should be in connection with the electric circuit and should extend up through the upper surface of the unit so that it can be turned on and off by manual activation by one on the upper side of the unit. This will help cut off power should an emergency arise or to restart the unit should the probe go out for any reason.

Since such a UV probe could go out, a service person or, perhaps the owner, could periodically check to see whether the probe is on by looking at the sensor and determining whether the probe is on by the light coming, or not coming, through the sensor as the case may be.

It is preferred that the type of UV sterilizing bulb used in connection with the apparatus should be a double tube lamp having electrical contacts at one end only. They may be described as "single ended" and "double tube." Such bulbs are distinguished over those with a "U" shape.

Such lamps are known in the field and may be described as having a pair of single ended lamps. The lamps may be described as consisting of two narrow fluorescent tubes, welded or otherwise attached together. Commonly used tube diameters are roughly on the order of 16 mm. or thereabouts. Such lamps can operate on those ballast type of circuits that are widely known in the art. Such state of the art bulbs may typically come in sizes e.g. 4", 8" or 16" long. Each of the lamps may be connected to one another by a "bridge" that is known in the art. Such bridge is typically found at or near the "free end" of the lamps (i.e. that end that does not have the electrical connections).

Because the lamps are one sided, they have electrical contacts at one end of the lamp unit only so that they do not lead an additional electrical contact at the other end. This allows one end of the bulb to stand clear of the unit and so projecting the UV radiation into the duct or other area.

In addition, the invention contemplates a method of increasing the efficacy of the sterilizing unit by lining the inside surfaces of the ducts in the home or building that leads to the sterilizing unit with a reflective material. The preferred reflective material would be e.g. aluminum foil or aluminum sheet material as it is believed that this material would be cost effective for this purpose and appears to have the necessary reflective properties in order to increase the propagation of the sterilizing light and hence distribute this light more effectively through the duct system. Other types of aluminum or aluminum coated material may be used without varying from the spirit of the invention.

The unit described herein may find use in heating, ventilation, and air conditioning ducts as well as filters, air handlers, electronic air filters and air returns.

I claim:

1. A sterilizing unit for air ducts comprising: a housing of substantially rectangular shape and cross section, said housing having side walls, an upper flange and an underside so as to enclose an area, said housing comprising aluminum material and said upper flange overhanging said side walls of said housing, a UV emitting means in connection with said housing, said housing having a passageway in said underside for said UV emitting means to extend through; an electrical power circuit in connection with said UV emitting means, said electrical circuit secured inside said housing, a sensor comprising light transmissive material in connection with said housing, said sensor extending from said upper flange to said underside, said sensor in close proximity to said UV emitting means so as to provide a visual indication of the condition of said UV emitting means; wherein said UV emitting means is of a double tube, single ended design having electrical connections for said tube at said single end.

2. A method of sterilizing air ducts that comprise a passageway having at least one end and having an inside surface; the method comprising: lining a substantial area of said inside surface with aluminum foil; placing a UV emitting bulb in connection with said end of said air duct.

* * * * *